US010750997B2

(12) United States Patent
Pernu et al.

(10) Patent No.: US 10,750,997 B2
(45) Date of Patent: Aug. 25, 2020

(54) BIOMETRIC SENSOR PACKAGE FOR INTEGRATION WITH A GARMENT

(71) Applicant: Suunto Oy, Vantaa (FI)

(72) Inventors: Kimmo Pernu, Vantaa (FI); Mikko Martikka, Vantaa (FI); Andrea Hartleb, Metz-Tessy (FR)

(73) Assignee: Suunto Oy, Vantaa (FI)

( * ) Notice: Subject to any disclaimer, the term of this patent is extended or adjusted under 35 U.S.C. 154(b) by 451 days.

(21) Appl. No.: 14/326,514

(22) Filed: Jul. 9, 2014

(65) Prior Publication Data

US 2016/0007919 A1 Jan. 14, 2016

(30) Foreign Application Priority Data

Jul. 9, 2014 (FI) ...................................... 20145666

(51) Int. Cl.
*A61B 5/0402* (2006.01)
*A61B 5/04* (2006.01)
(Continued)

(52) U.S. Cl.
CPC .......... *A61B 5/6804* (2013.01); *A61B 5/0245* (2013.01); *A61B 5/0478* (2013.01);
(Continued)

(58) Field of Classification Search
CPC .......... D04B 1/14; D04B 1/123; D04B 1/246; A61B 5/04085; A61B 5/6804;
(Continued)

(56) References Cited

U.S. PATENT DOCUMENTS

| 4,248,247 A * | 2/1981 | Ware ................... A61N 1/0492 |
| | | 252/519.21 |
| 2006/0142654 A1 | 6/2006 | Rytky |

(Continued)

FOREIGN PATENT DOCUMENTS

| EP | 2505090 A2 | 10/2012 |
| EP | 2654030 A1 | 10/2013 |

(Continued)

*Primary Examiner* — Eun Hwa Kim
*Assistant Examiner* — Brian M Antiskay
(74) *Attorney, Agent, or Firm* — Laine IP Oy

(57) ABSTRACT

Described herein is a biometric sensor package. In particular, a biometric sensor package for integration with a garment. Furthermore, methods of manufacturing of such biometric sensor packages are disclosed. Still yet, methods of integrating biometric sensor packages in to garments are disclosed. The biometric sensor packages described herein can easily be manufactured by current biometric sensor manufactures, for example heart rate monitor belt manufacturers. The biometric sensor packages described here can then be easily integrated in to garments by current garment manufacturers without requiring any special knowledge or tooling relating to the actual biometric sensor arrangements within the biometric sensor packages. Through the use of biometric sensor packages described herein biometric sensor arrangements, such as heart rate monitors and EEG sensors can be easily integrated into garments, such as sports bras, shirts and shorts, without disrupting existing supply chains and factories.

12 Claims, 5 Drawing Sheets

(51) Int. Cl.
*A61B 5/00* (2006.01)
*A61B 5/0245* (2006.01)
*A61B 5/0492* (2006.01)
*A61B 5/0478* (2006.01)

(52) U.S. Cl.
CPC ..... *A61B 5/0492* (2013.01); *A61B 2560/0412* (2013.01); *A61B 2562/164* (2013.01); *A61B 2562/242* (2013.01)

(58) Field of Classification Search
CPC ... A61B 5/6805; A61B 5/0408; A61B 5/6831; A61B 5/02438; A61B 5/0006; A61B 5/0402; A61B 2560/0468; A61N 1/0484; A61N 1/0492; A61N 1/0452; A61N 1/0472; A41D 13/1281; D10B 2403/02431; D10B 2501/00
USPC ....... 600/372, 382, 384, 386, 388–391, 393, 600/508–509
See application file for complete search history.

(56) References Cited

U.S. PATENT DOCUMENTS

| | | | |
|---|---|---|---|
| 2007/0285868 A1* | 12/2007 | Lindberg | A61B 5/0245 600/382 |
| 2008/0143080 A1* | 6/2008 | Burr | D04B 1/14 280/495 |
| 2008/0255649 A1 | 10/2008 | Herbert | |
| 2009/0203984 A1* | 8/2009 | Dias | A61B 5/6804 600/388 |
| 2009/0227856 A1* | 9/2009 | Russell | A41D 13/1281 600/388 |
| 2010/0324405 A1* | 12/2010 | Niemi | A61B 5/0408 600/396 |
| 2013/0338471 A1* | 12/2013 | Huang | A61B 5/02444 600/386 |
| 2014/0150573 A1 | 6/2014 | Cannard et al. | |

FOREIGN PATENT DOCUMENTS

| | | |
|---|---|---|
| EP | 2695575 A1 | 2/2014 |
| WO | WO2006064447 A2 | 6/2006 |
| WO | WO2010101633 A2 | 9/2010 |

\* cited by examiner

BIOMETRIC SENSOR PACKAGE FOR INTEGRATION WITH A GARMENT

FIELD OF INVENTION

The present application is generally directed to biometric sensor packages. More particularly, to biometric sensor packages for integration with a garment. Additionally, methods of manufacturing biometric sensor packages and integrating them with a garment are disclosed.

BACKGROUND OF INVENTION

Biometric sensors, such as heart rate monitors and EEG monitors, are becoming ever more popular amongst the general population. Heart rate monitor belts in particular are wide spread with people utilizing them in a variety of activities from walking to running, cycling, swimming and while playing sports. Current heart rate monitor belts are limited to actual belts which need to be worn by a user directly on the skin, typically underneath an athletic top.

It has long been a desire of users to have heart rate monitor belts integrated in to garments, e.g. sports bras, shirts and compression tops. However, many practical problems have kept heart rate monitor belts out of garments. One of the key practical factors deals with the current manufacturing supply chain. Most actual garments are constructed by garment manufacturers using specialized equipment, e.g. commercial sewing machines. These garment manufacturers are only equipped for the assembly of garment pieces, e.g. adding sleeves to a torso to form a shirt. They are not equipped to add electronics to garment pieces.

In order to manufacture a heart rate monitor belt typically two electrodes need to be affixed to some material in a precise manner. This is due to the contacts of the electrodes needing to be in a very specific orientation with respect to each other so that a telemetric electronic device can be releasable connected to the contacts and the telemetric electronic device typically has male snap portions at a predefined and fixed distance from each other.

To simply manufacture a heart rate monitor belt in to a garment would require the re-tooling of an existing manufacturer in the supply chain or the building of an entirely new manufacturing chain. For example, either the garment manufacturer would need to add space to the equipment needed to align and affix the electrodes to a garment during the garment assembly, or the heart rate monitor manufacturer would need to add all of the processes required for garment assembly. Neither is a feasible solution and thus heart rate monitor sensors have been relegated to their own belts.

Therefore, there exists a need for a product and method which allows for the integration of a biometric sensor in to a garment without the need for significantly altering current well established supply chains in either the garment or electronics manufacturing industries.

SUMMARY OF THE INVENTION

Described herein is a biometric sensor package. In particular, a biometric sensor package for integration with a garment. Furthermore, method of manufacturing of such biometric sensor packages are disclosed. Still yet, methods of integrating biometric sensor packages in to garments are disclosed.

According to certain embodiments, there is disclosed a biometric sensor package which comprises a biometric sensor arrangement which is sandwiched between two material layers. The material layers may be flexible material layers. Additionally, the biometric sensor arrangement includes a material allowance. The material allowance can be for integrating the biometric sensor package with a garment. The material allowance can also be for integrating the sandwiched biometric sensor arrangement to a garment.

According to certain examples, the two material layers are an integral piece. The integral piece can be a single material and the two material layers can be separate portions of the single material. The integral piece can also be two different material layers which have been affixed to each other, e.g. by sewing, adhesive or heat welding.

According to certain examples, a portion of at least one of the flexible material layers forms at least a portion of the material allowance. The material allowance may be formed by only one of the flexible material layers or by both. The material allowance may also be formed, in whole or in part, by an addition material which is affixed to one or more of the flexible material layers.

A biometric sensor package as described herein can be for integration within a garment. A biometric sensor package as described herein can also be integrated within a garment. The biometric sensor package can be integrated within a garment as a piece of a garment. As a piece of a garment it can be integrated in any fashion as any other garment piece in a garment manufacturing process, e.g. sewing. The biometric sensor package can be sewn, for example, by sewing the material allowance of the biometric sensor package to a material allowance of at least one other portion of a garment. Such methods of integration can be carried out using existing machinery by a garment manufacturers and typically does not require any modification to the garment manufacturers machinery.

Described herein are also methods of manufacturing the disclosed biometric sensor packages. Such methods can include the steps of placing a biometric sensor arrangement on a first flexible material layer and placing a second flexible material layer such that the biometric sensor arrangement is sandwiched between the flexible material layers.

Described herein are also methods of integrating the described biometric sensor packages into garments. Such methods may include affixing at least one of the material layers of the biometric sensor package to a portion of a garment.

BRIEF DESCRIPTION OF THE DRAWINGS

FIG. 1b shows an open view of the biometric sensor package of FIG. 1a.

DETAILED DESCRIPTION OF EXAMPLE EMBODIMENTS

Figure 1A:
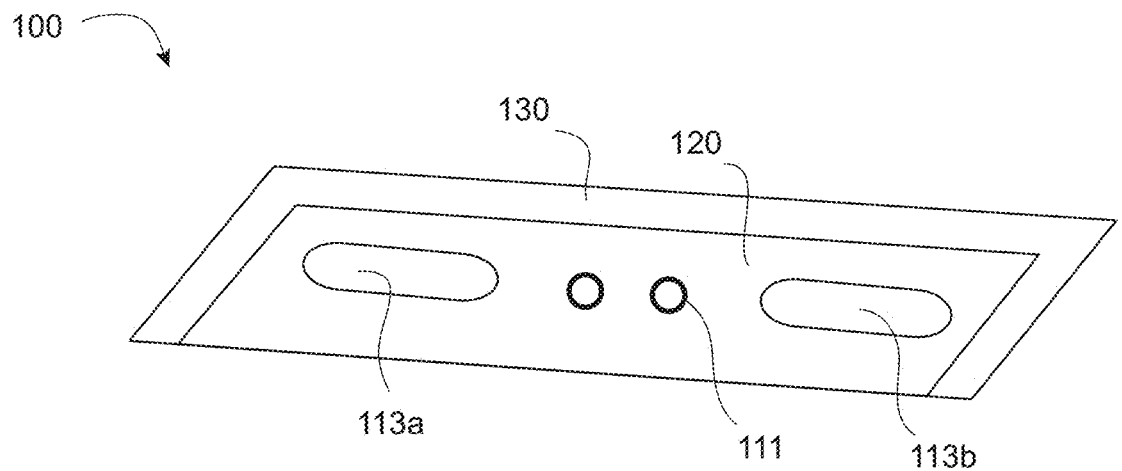
FIG. 1a shows an example of a biometric sensor package.

FIG. 1A is an example of a biometric sensor package embodiment of the invention. The biometric sensor package 100 of FIG. 1 has a sensor arrangement. The sensor arrangement can be a biometric sensor arrangement, for example, for monitoring heart rate, EEG or muscle activity. The sensor arrangement shown in the example of FIG. 1 is arranged for monitoring heart rate via sensor pads 113a and 113b. The sensor arrangement further can include, for example, a coupler 112. The coupler 112 can couple multiple sensors or sensor pads, e.g. 113a and 113b, and/or providing a connection point between one or more sensors and a separable electronic module. Furthermore the invention is not limited to the specific sensor arrangements disclosed herein as other types of sensor arrangements can be used together with the present invention without departing from the scope of the present invention.

The biometric sensor arrangement in the present example is sandwiched between layers of material. In FIG. 1 the front material layer 120 is shown. Material layers which sandwich the biometric sensor arrangement may be flexible. Additionally, each the material layer may be made up of more than one piece of material. The multiple pieces of material of a single material layer may be, for example, stacked, overlapping, or attached next to but not overlapping each other. Multiple pieces of material of a single material layer may be different pieces of the same materials including, for example: fabric, polymer and metal. Multiple pieces of material of a single material layer may also be of different materials from each other.

The biometric sensor package 100 further includes a material allowance 130. The material allowance can be for integration of the biometric sensor package with another object. The object can typically be a garment. Examples of such garments are: a shirt, a bra, compression shorts and shirts, belts, and shoes. The material allowance can also provide for integration with additional material. Additional material may be, for example, a belt, a portion of a garment or other fabric.

According to certain examples, a portion of at least one of the material layers 120 forms at least a portion of the material allowance 130. A portion of at least one of the flexible material layers 120 may also form the entire material allowance 130. The material allowance 130 may be formed from a material separate from and affixed to the material layers. The material allowance may be, for example, affixed between the material layers. The material allowance may also be affixed to a portion of at least one material layer.

Figure 1B:
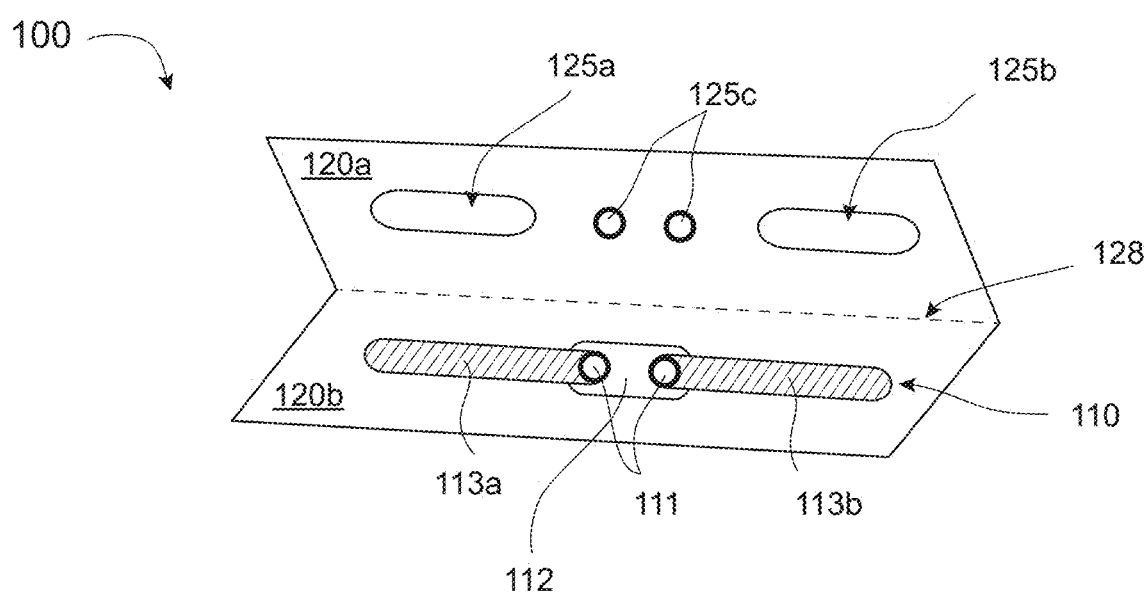

FIG. 1B illustrates an open example biometric sensor package 100. In FIG. 1b the sensors pads 113a and 113b of the biometric sensor arrangement are shown as affixed to the coupler 112. In certain examples of the present invention the coupler may use snaps 111. The biometric sensor arrangement may be sandwiched between two flexible material layers 120a and 120b. In this example the two material layers 120a and 120b are an integral piece. The two material layers 120a and 120b may be formed from one piece of flexible material 220, for example which is folded to form the two material layers. FIG. 2 shows a crease line 128 separating the first and second material layers.

The two material layers may also be formed into an integral piece via coupling more than one piece of material. The multiple pieces of material of the integral piece may be, for example, stacked, overlapping, or attached next to but not overlapping each other. Multiple pieces of material may be different pieces of the same materials including, for example: fabric, polymer and metal. Multiple pieces of material of the integral piece may also be of different materials from each other.

It may be beneficial to have holes (125a, 125b, 125c) within at least one of the flexible material layers 120a. The holes may be formed by removing fabric of a material layer. The holes may be formed via joining multiple pieces of material. While the holes may be beneficial, they are not necessary for the present invention. The holes may be areas of material different from the material of the material layer having holes.

Examples of the present invention also have an adhesive layer. The adhesive layer may be placed and disposed in various fashions. Certain examples of the present invention have an adhesive layer at least partially surrounding a biometric sensor arrangement. As discussed herein, surrounding means substantially surrounding the biometric sensor arrangement. This surrounding may be accomplished by placing a plurality of lines of adhesive surrounding the biometric sensor arrangement. Surrounding may also mean a line of adhesive drawn around the biometric sensor arrangement. The line of adhesive may be continuous or non-continuous. The adhesive layer may surround the biometric sensor by being spread across at least a portion of a material layer. The adhesive layer may also cover all of a material layer.

Adhesives suitable for use with flexible materials may be used in the adhesive layer. Multiples adhesives may be used in the adhesive layer. In certain examples of the present invention, adhesive which can be heat set is used.

An adhesive layer may be used to couple at least a portion of the material layers to another portion of the material layers. Additionally the adhesive layer may be used to couple a biometric sensor arrangement to at least a portion of the two flexible material layers.

In certain examples of the present invention, adhesive is applied to the flexible material layer. The biometric sensor arrangement is placed on the adhesive layer. Then the biometric sensor arrangement may be sandwiched between flexible material layers by affixing another flexible material layer atop a portion of the allowance.

FIGS. 2A-2E illustrate various examples of arrangements of the material allowance 230. As shown, the material allowance 230 may be arranged as suitable for integration with various items. The material allowance 230 may be a material affixed to at least one of the flexible material layers 220.

The adhesive layer may not cover the entire flexible material layer. In certain examples of the present invention at least one edge portion of at least one of the flexible material layers is free of adhesive of the adhesive layer. The material allowance may be at least partially formed by the edge portion free of adhesive. Furthermore, the area free of adhesive may make up at least a portion of the material allowance. Additional edge portions may be left free of adhesive as necessary.

Within certain examples of the present invention it is beneficial to have a material allowance with a minimum width. This minimum width can be defined such that it may be easily manipulated by standard commercial equipment. This manipulation may include sewing. In certain examples of the present invention it is beneficial that the material allowance have a minimum width such that it can be used for affixing the biometric sensor package to a garment using standard commercial equipment. This affixing may be, for example, sewing. A minimum width of at least 1 centimeter may be used. As mentioned, an edge portion free of adhesive may make up at least a portion of the material allowance. In certain embodiments it is therefore beneficial to have an edge portion free of adhesive of the adhesive layer measured from the edge of the flexible material layer to the center of the material which has a minimum width of at least 1 centimeter.

Figure 2A:
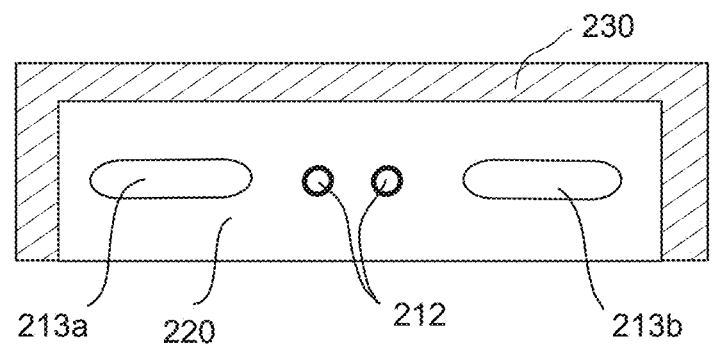
FIGS. 2a-2e show examples of biometric sensor packages with different material allowances.

FIG. 2A illustrates a material allowance 230 which is three edge portions of the flexible material layer 220. In certain examples of the present invention the material allowance may be at least one edge portion of the flexible material layer. The sensor pads (213a, 213b) and coupler 212 of the biometric sensor arrangement are also shown. Portions of the biometric sensor arrangement may be sandwiched within the flexible material layers with only one material layer 220 shown. This can be formed, for example, by having two separate material layers, wherein one of the material layers has an area smaller than the other. As a further example the material allowance 230 may also be formed by affixing a material to the material layer 220. In such an example the material which forms the material allowance could be shaped to be just larger than the material layer. The material which forms the material allowance could also be shaped to match the shape of the material allowance. Such a material which forms the material allowance could itself have a material allowance for affixing to the material layer 220.

As previously mentioned, the material allowance may be formed of edge portions of the flexile material layers which are free of adhesive. Certain examples of the present invention would have at least one edge portion free of adhesive. This could include at least three edge portions free of adhesive.

Figure 2B:
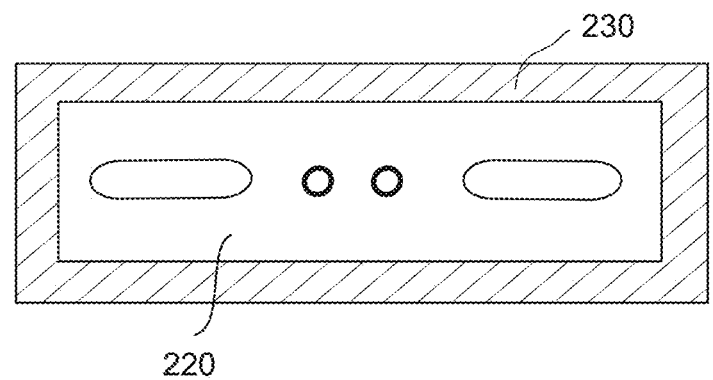

FIG. 2B illustrates a material allowance 230 which completely surrounds the sandwiched biometric sensor arrangement. This can be formed, for example, by having two separate material layers 220 and 230, wherein one of the material layers has an area smaller than the other. The material layer with the smaller area may be completely affixed to the larger material layer. In such an example, the material allowance 230 would be formed only from a portion of one of the material layers, i.e. the larger material layer. The material with the smaller area may also be affixed in another manner, for example as described with regards to the other figures. For example, one or more edges of the smaller material layer may be left free of adhesive such that a portion of the smaller material layer together with a larger portion of the larger material layer form the material allowance. According to such an example, material can be economized by not having two portions of excess material forming the whole material allowance.

Figure 2C:
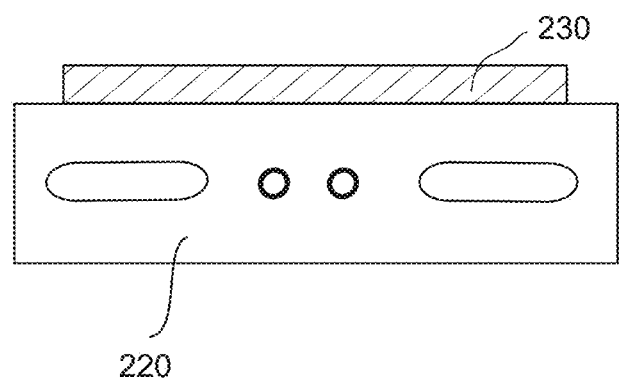

FIG. 2C illustrates a material allowance 230 which is not the full width of at least one of the flexible material layers. This example of the present invention may be beneficial when affixing a material to act as the material allowance. The material allowance 230 may be formed by affixing a piece of material to at least one of the material layers prior to coupling the material layers. The material allowance 230 may also be formed via placing a material between the material layers prior to curing an adhesive layer. In such an example the components of the biometric sensor package would be arranged as desired and then an adhesive layer cured only once.

Figure 2D:
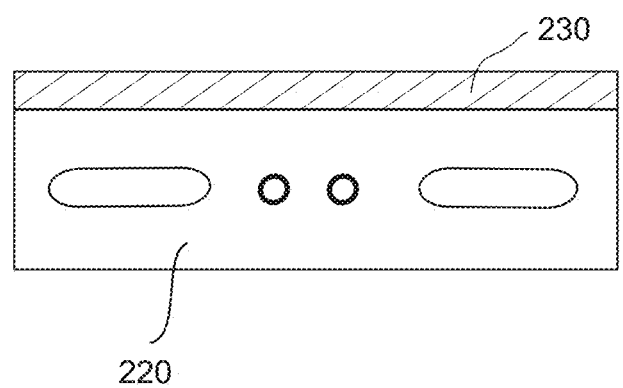

FIG. 2D illustrates a material allowance 230 along only one side of the sandwiched biometric sensor arrangement. The material allowance 230 as illustrated in FIG. 2D may be formed by affixing a material to any portion of the material layers. The material allowance may also be formed as previously mentioned via material layers which are of different sizes.

Figure 2E:
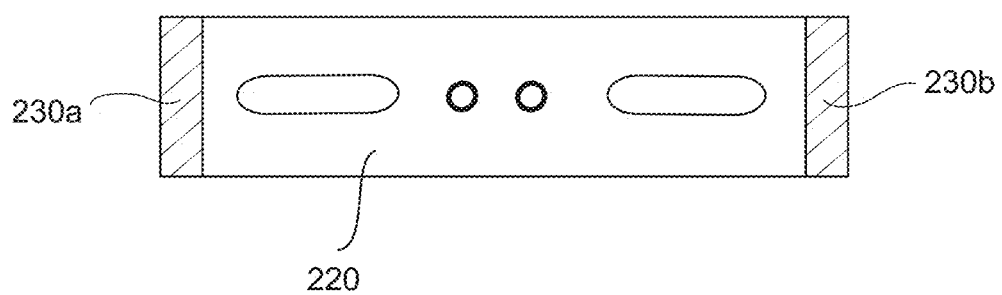

FIG. 2E illustrates a material allowance 230a and 230b which is two portions on opposite sides of the sandwiched biometric sensor arrangement.

Figure 3:
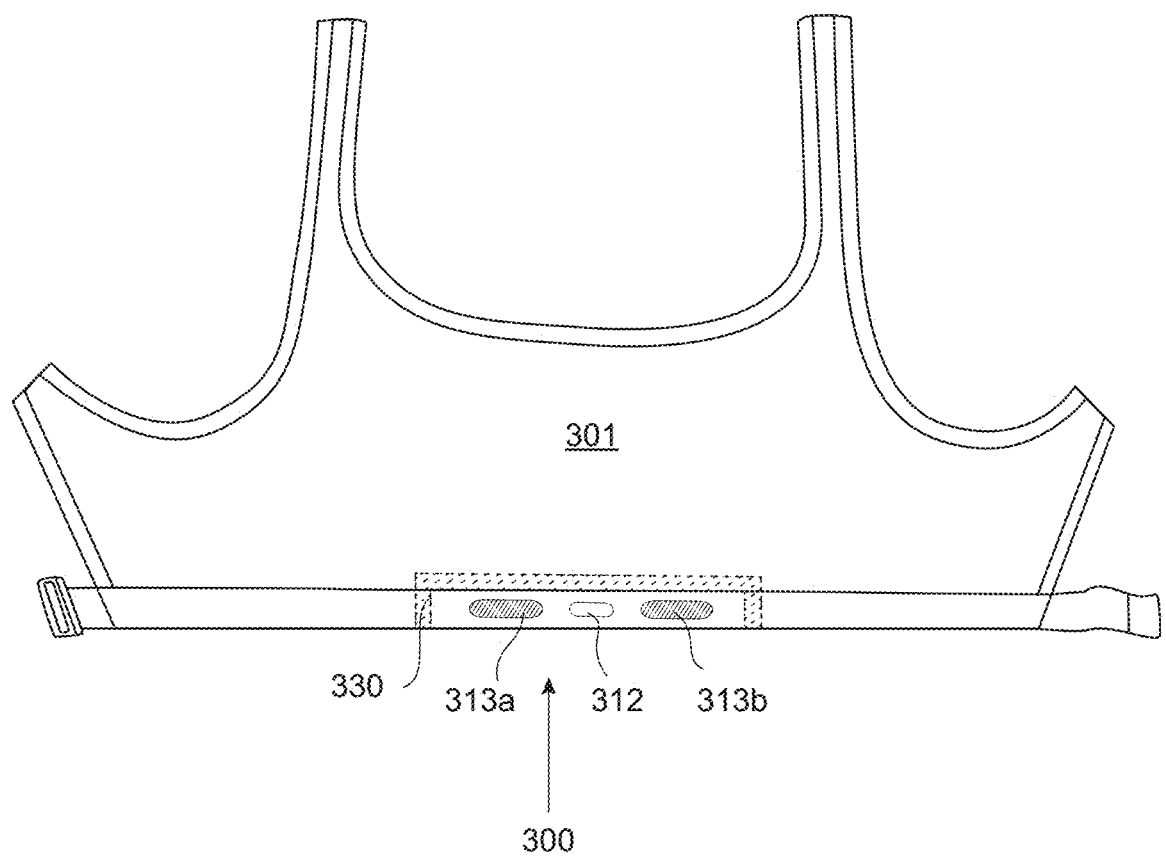
FIG. 3 shows an example of a sports bra having a biometric sensor package.

FIG. 3 illustrates an example of the present invention integrated within a garment 301. The biometric sensor package 300 is integrated with the garment via the material allowance 330. The material allowance may be affixed to the garment 301, for example, via stitching or sewing. The biometric sensor package 300 may be affixed to the garment 301 via the material allowance 330 in other manners as well. For example an adhesive could be added to the material allowance 330. The adhesive may be a part of the previously mentioned adhesive layer or a different adhesive. The adhesive may be activated via chemically, thermally, or mechanically. Such an adhesive would allow the biometric sensor package to be affixed to a garment when heated, for example, via a heat press.

Within the example of FIG. 3 one material layer 320 is shown. This material layer is just one of the layers which have sandwiched the biometric sensor arrangement. Portions of the biometric sensor arrangement shown in FIG. 3 include: sensor pads 310a and 310b and a coupler 312. The coupler 312 may allow coupling of a heart rate, EEG or muscle activity monitor. The couple may also allow coupling of a transmitting unit.

Figure 4:
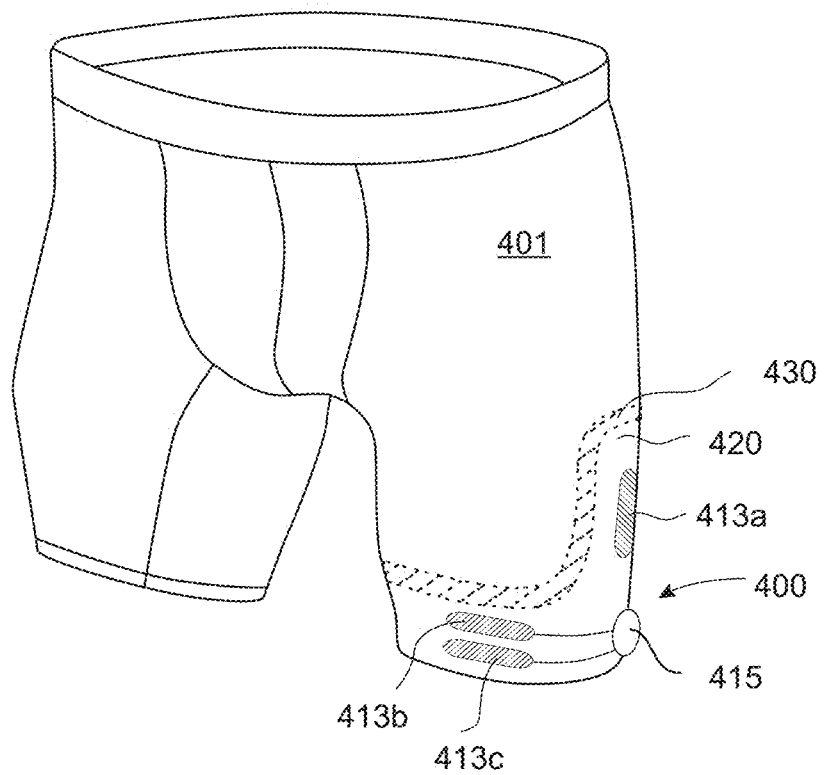
FIG. 4 shows an example of shorts having a biometric sensor package.

FIG. 4 illustrates an example embodiment of the present invention. In this example a garment 401 is shown having an integrated sensor package 400. In this example three sensor pads 413a, 413b, and 413c of the biometric sensor arrangement are shown. Attached to the biometric sensor arrangement is an electronic device 415. This device may be a transmitting or monitoring device. In this example, the material allowance 430 allows the biometric sensor package to be affixed to the garment. The biometric sensor package may be affixed to the garment via a stitch-less seam. Within the illustrated example embodiment the sensor pads are arranged to detect muscle activity.

In certain examples of the present invention the material allowance may be at least partially made of material of the flexible material layer. Additionally a piece of material affixed to at least one of the flexible material layers sandwiching the biometric sensor arrangement could make up at least a portion if not all of the material allowance.

The biometric sensor package as described above can be manufactured with existing machinery and processes by current biometric sensor manufacturing companies. For example, a company manufacturing current heart rate monitor belts can, without much infrastructure change, manufacture a biometric sensor arrangement as described herein. However, the resultant biometric sensor arrangement as described herein is particularly well suited to be then integrated into a garment.

A biometric sensor package as described herein can be manufactured by either placing or arranging a biometric sensor arrangement on a first material layer. The first material layer can be flexible. The first material layer may be the same material as a material of a garment for which the biometric sensor package is to be integrated. A second material layer can be then added which sandwiches the biometric sensor arrangement between said second material layer and the first material layer.

The second material layer can be similar or different to that of the first material layer. For example, if a biometric sensor package is to be integrated into a garment having an inner material and a different outer material, then the first and second material layers could correspond to the different materials of the eventual garment which will have the biometric sensor package. In such examples the first and second material layers may be separate until they are placed together, sandwiching the biometric sensor arrangement. The first and second material layers may also have been pre-joined, e.g. sewn together, and then the second material layer could have been folded, for example either at or near the joining, over the first material layer having the biometric sensor arrangement.

The second material layer may also be a portion of the first material layer. If only a single material type is desired then the biometric sensor arrangement can be arranged on a first portion of a material layer and then another portion of the same material layer can be arranged over the first portion and the biometric sensor arrangement. The first portion of the material layer would then form the first material layer and the second portion of the same material layer would form the second material layer.

An adhesive layer can be placed between at least a portion of the first material layer and at least a portion of the second material layer. An adhesive layer can be placed between at least a portion of the first material layer and the biometric sensor arrangement. The same adhesive layer may be between the first material layer and both the second material layer and the biometric sensor arrangement. The adhesive layer may be cured as well, affixing the multiple parts together.

One or more material allowances of the biometric sensor package can be formed by the absence of an adhesive layer between portions of the first and second material layers. For example, if the first and second material layers are formed from the same flexible material layer which is folded over a biometric sensor arrangement, then an adhesive layer can be added between the first and second material layers. If the adhesive layer is smaller does not extend to at least one edge of one of the material layers then a material allowance will be formed. According to certain examples, the adhesive layer does not extend to any of the free edges of either the first nor second material layers. By free edge it is meant an edge which is not otherwise connected to another material layer. In an example such as 100 of FIG. 1a, three free edges of the material layers are free from adhesive and form a material allowance which wraps around three edges of the overall biometric sensor package.

A biometric sensor package as described herein can then be integrated as a garment piece into a garment by a garment manufacturer. A garment manufacturer can treat the biometric sensor package as any other garment piece, e.g. like a sleeve, and can integrate the biometric sensor package into the garment by, for example, sewing in the biometric sensor package into a garment.

FIG. 3 shows an example of a biometric sensor package which has been sewn into a bottom portion of a sports bra. The biometric sensor package can form a portion of a bottom portion of the sports bra as shown. A biometric sensor package may also form an entire lower band portion of a garment, such as a sports bra. The material for one or more of the material layers may be particularly well suited to act as the lower band of the garment. For example, it may be of an elastic, or more elastic material compared to the material of the remainder of the garment. In that way, the biometric sensor package may make up a structural portion of the garment to which it is integrated, or to be integrated. A similar example is shown in FIG. 4 where the biometric sensor arrangement forms an integral portion of the leg of the shorts.

As described herein, a biometric sensor package can now be manufactured in more or less the same supply chain as currently exists for heart rate monitor belts. The biometric sensor package can then be integrated in to a garment in the same supply chain as currently exists for garment manufacturing, without the garment manufacturers needing to take any responsibility for the actual arrangement of the biometric sensor arrangement within the garment. Thus, biometric sensors can be integrated into garments without disrupting any existing supply chain.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

Certain embodiments of the invention are produced by first placing a biometric sensor arrangement on a first flexible material layer. Then a second flexible material layer is placed such that the biometric sensor arrangement is sandwiched between flexible material layers. The first and second flexible material layers may be an integral. In embodiments where the flexible material layers are integral, the two layers may be caused to sandwich the biometric sensor arrangement via a folding action.

In some embodiments of the present invention an adhesive layer is utilized. The adhesive layer provides for more support for the sensor arrangement and allows for greater durability. When an adhesive layer is used it is placed between at least a portion of the first flexible material layer and at least one of: a portion of the second flexible material layer and the biometric sensor arrangement. This adhesive layer may be cured.'

In certain embodiments of the present invention it is beneficial to affix additional material to at least one flexible material layer. In these embodiments the additional material may server as a material allowance. The material allowance may allow for affixing the biometric sensor package to a garment.

The invention claimed is:

1. A wearable biosensor device comprising:
a garment;
a biometric sensor arrangement comprising:
two electrodes for physiological monitoring:
two flexible superimposed material layers formed by folding a piece of material a single time, wherein the two flexible superimposed material layers comprise a plurality of perimeter edges, wherein the two electrodes are disposed on one of the two flexible superimposed material layers so that the electrodes are sandwiched between the two flexible superimposed material layers; and
a material allowance disposed on at least one of the perimeter edges of the two flexible superimposed material layers;
wherein the biometric sensor arrangement is attached to the garment by affixing a surface of the material allowance to a surface of said garment.

2. The wearable biosensor device of claim 1, wherein the material allowance is at least a portion of at least one of the flexible superimposed material layers.

3. The wearable biosensor device of claim 1, wherein at least a portion of the material allowance is an additional material affixed to at least one of the flexible superimposed material layers.

4. The wearable biosensor device of claim 1, further comprising an adhesive layer coupling at least a portion of the two flexible superimposed material layers to each other.

5. The wearable biosensor device of claim 4, wherein at least one of the plurality of perimeter edges of at least one of the flexible superimposed material layers is free from adhesive.

6. The wearable biosensor device of claim 5, wherein the material allowance is at least partially formed by the at least one of the plurality of perimeter edges of at least one of the flexible superimposed material layers free from adhesive.

7. The wearable biosensor device of claim 4, wherein at least three edges of the plurality of perimeter edges are free of adhesive of the adhesive layer.

8. A method for integrating electrodes for physiological monitoring into a garment, comprising the steps of:
providing two electrodes for physiological monitoring,
folding a piece of flexible material around the two electrodes a single time such that two flexible superimposed material layers are formed, wherein the two electrodes are disposed on one of the two flexible superimposed material layers so that the electrodes are sandwiched between the two flexible superimposed material layers, wherein the two flexible superimposed material layers comprise a plurality of perimeter edges
disposing a material allowance on at least one of the perimeter edges of the two flexible superimposed material layers, and
affixing a surface of the material allowance to a surface of a garment to integrate the two electrodes into said garment.

9. The method of claim 8 wherein the material allowance is affixed to the garment via sewing.

10. The method of claim 8 wherein the garment is a sports bra, shirt, compression shirt, shorts, compression shorts, pants, compression pants or undergarment.

11. The method of claim 8, wherein the material allowance is at least a portion of at least one of the flexible superimposed material layers.

12. The method of claim 8, wherein at least a portion of the material allowance is an additional material affixed to at least one of the flexible superimposed material layers.

* * * * *